United States Patent
Volmer et al.

(10) Patent No.: US 11,690,968 B2
(45) Date of Patent: Jul. 4, 2023

(54) BREATHING AIR SUPPLY SYSTEM WITH CONTACTLESS VITAL PARAMETER SENSOR MEASURING

(71) Applicant: Dräger Safety AG & Co. KGaA, Lübeck (DE)

(72) Inventors: Achim Volmer, Lübeck (DE); Alexander Korff, Lübeck (DE)

(73) Assignee: Dräger Safety AG & Co. KGaA, Lübeck (DE)

(*) Notice: Subject to any disclaimer, the term of this patent is extended or adjusted under 35 U.S.C. 154(b) by 525 days.

(21) Appl. No.: 16/864,777

(22) Filed: May 1, 2020

(65) Prior Publication Data

US 2020/0353194 A1    Nov. 12, 2020

(30) Foreign Application Priority Data

May 2, 2019  (DE) .......................... 102019003086.9

(51) Int. Cl.
    *A61M 16/06*    (2006.01)

(52) U.S. Cl.
    CPC ..... *A61M 16/0666* (2013.01); *A61M 2205/18* (2013.01); *A61M 2205/3317* (2013.01); *A61M 2205/3553* (2013.01); *A61M 2205/3592* (2013.01); *A61M 2209/088* (2013.01)

(58) Field of Classification Search
    CPC .... A62B 9/00; A62B 9/02; A62B 9/04; A62B 9/006; A62B 7/00–12; A62B 18/02; G08B 21/0438; G08B 21/0453; G08B 21/0469; G08B 21/0476; G08B 21/0484; G08B 21/0492; B63C 11/22; A61B 5/00–0008; A61B 5/0015; A61B 5/0024; A61M 2209/088
    See application file for complete search history.

(56) References Cited

U.S. PATENT DOCUMENTS

| | | | |
|---|---|---|---|
| 4,875,477 A | 10/1989 | Waschke et al. | |
| 5,949,337 A * | 9/1999 | Campman ............... | G08B 21/02 128/204.23 |
| 8,773,269 B2 | 7/2014 | Richardson | |
| 9,044,625 B2 * | 6/2015 | Palacharla ............. | A62B 9/006 |
| 9,414,784 B1 * | 8/2016 | Berme ..................... | A61B 5/01 |
| 2009/0023421 A1 * | 1/2009 | Parkulo ............. | G08B 21/0415 455/556.1 |
| 2016/0059048 A1 | 3/2016 | Kanakala et al. | |
| 2016/0331249 A1 * | 11/2016 | Lee ..................... | A61B 5/7225 |

(Continued)

FOREIGN PATENT DOCUMENTS

| | | |
|---|---|---|
| DE | 3724336 A1 | 2/1989 |
| DE | 102009033828 A1 | 1/2011 |

(Continued)

*Primary Examiner* — Joseph D. Boecker
*Assistant Examiner* — Thomas W Greig
(74) *Attorney, Agent, or Firm* — McGlew and Tuttle, P.C.

(57) ABSTRACT

A breathing air supply system (200) is configured to be carried by a person (300) and includes a breathing air supply device (130), a fastening device (1) for the breathing air supply device (130) and a vital parameter sensor (30.1). The vital parameter sensor (30.1) is mounted in or at a back section (22) belonging to a fastening section (20) of the fastening device (1). The vital parameter sensor (30.1) is configured to contactlessly measure a vital parameter of a user (300) of the breathing air supply system (200).

15 Claims, 4 Drawing Sheets

(56) References Cited

U.S. PATENT DOCUMENTS

| | | | |
|---|---|---|---|
| 2016/0379473 A1 | 12/2016 | Bharti et al. | |
| 2017/0072231 A1* | 3/2017 | Carr | G08B 25/00 |
| 2017/0172425 A1* | 6/2017 | Liu | A61B 5/05 |
| 2017/0270775 A1 | 9/2017 | Haase | |
| 2017/0296094 A1* | 10/2017 | Fonzi, III | A61B 5/0002 |

FOREIGN PATENT DOCUMENTS

| | | |
|---|---|---|
| DE | 102016116761 A1 | 3/2017 |
| ES | 2343398 A1 | 7/2010 |
| WO | 2017181157 A1 | 10/2017 |

\* cited by examiner

BREATHING AIR SUPPLY SYSTEM WITH CONTACTLESS VITAL PARAMETER SENSOR MEASURING

CROSS REFERENCE TO RELATED APPLICATIONS

This application claims the benefit of priority under 35 U.S.C. § 119 of German Application 10 2019 003 086.9, filed May 2, 2019, the entire contents of which are incorporated herein by reference.

TECHNICAL FIELD

The present invention pertains to a breathing air supply system with a breathing air supply device, with a fastening device for the breathing air supply device and with at least one vital parameter sensor, which is arranged at or in the fastening device and monitors a vital function of a user of the breathing air supply system.

TECHNICAL BACKGROUND

A portable respirator supplies a person, who carries this respirator, with breathing air. This person will hereinafter be called "the user". Thanks to the respirator, the user does not need to inhale the ambient air and can therefore work in a surrounding area in which the ambient air is or may be enriched with harmful substances.

Different portable respirators have become known.

A portable belt device for a breathing air supply device is described in DE 10 2016 116 761 A1. A housing accommodates the majority of the components of the breathing air supply device and comprises a front housing element and a rear housing element. A left shoulder strap and a right shoulder strap are fastened at the front housing element. A telemetry module is capable of transmitting the temperature and the heart rate of a rescue crew member, who carries the breathing air supply device, to a central control unit located remotely in space.

A breathing air supply device (self-contained breathing apparatus, SCBA 5) with a compressed air cylinder (pressurized air tank) is described in WO 2017/181157 A1. A carrier system with a back plate carries the compressed air cylinder. A sensor measures, for example, the body temperature, pulse rate, respiration rate or respiratory volume of a user of the breathing air supply device.

US 2016/0 059 048 A1 describes a breathing air supply device (self-contained breathing apparatus, SCBA) with a compressed air cylinder, wherein the breathing air supply device is fastened to a carrier system of a back plate (backpack). A personal safety system (Personal Alert Safety System, PASS) comprises a front pass with a first motion sensor and a back pass with a second motion sensor, wherein each motion sensor is capable of detecting whether a user of the breathing air supply device is still moving or not. The breathing air supply device and the two units are fastened to a mounting section of the carrier system.

DE 37 243 361 A1 describes a breathing air supply device with a gas mask, wherein the gas mask is held in a gastight manner in front of the face of a user. A sensor measures the heart rate of the mask user. A contact thermometer measures the body temperature. An optional sensor, not shown, measures the respiration rate or the breathing pressure. A sealing frame of the gas mask carries the sensor in the temporal region of the mask user and the contact thermometer on the opposite side.

The document ES 2 343 398 B1 discloses an article of clothing with a plurality of sensors. A radar sensor is used to detect a person approaching from behind.

US 2016/0 379 473 A1 discloses a sensor system, which calculates an "emergency level" on the basis of the detected data.

SUMMARY

A basic object of the present invention is to provide a breathing air supply system that can be carried by a person and is capable of detecting a change in a vital parameter, which change is hazardous for the user of the breathing air supply system, with a greater reliability than prior-art breathing air supply systems.

The breathing air supply system according to the present invention can be carried by a person, who will hereinafter be called the "user" of the breathing air supply system.

The breathing air supply system comprises
a breathing air supply device,
a fastening device and
at least one vital parameter sensor.

The breathing air supply device is capable of supplying the user with breathing air. The fastening device is configured to be in contact with the body of the user and to carry the breathing air supply device.

At least one vital parameter sensor is fastened at or in the fastening device or is integrated into the fastening device. This preferably applies to each vital parameter sensor.

The vital parameter sensor or each vital parameter sensor is capable of measuring at least one vital parameter of the user. Each measurable vital parameter is correlated with a vital function of the user.

The vital parameter sensor or each vital parameter sensor, preferably each vital parameter sensor, is capable of measuring a vital parameter in a contactless manner. The vital parameter sensor is capable of emitting electromagnetic waves in the direction of the body of the user and to receive and to analyze at least some of the emitted electromagnetic waves that are reflected from the body of the user. The vital parameter sensor is capable of measuring the respective vital parameter depending on the received electromagnetic waves.

The vital parameter sensor or a vital parameter sensor is fastened according to the present invention in or at the fastening device or is integrated into this. As a result, the vital parameter sensor is located in the vicinity of the user when the user is carrying the breathing air supply system and the fastening device is therefore in contact with the body of the user. It is not necessary for the user to put the vital parameter sensor or a vital parameter sensor on the body by a separate action. The present invention therefore avoids the unintended situation that the user forgets to put on the vital parameter sensor. In addition, the fastening device holds the vital parameter sensor in a desired position relative to the body of the user. The risk that the vital parameter sensor will become detached from the breathing air supply system by itself or based on an external mechanical effect and is no longer able to carry out the measurement is reduced.

The vital parameter sensor or at least one vital parameter sensor emits according to the present invention electromagnetic waves and measures the vital parameter as a function of the reflected and received electromagnetic waves. The breathing air supply system consequently measures the vital parameter in a contactless manner. Thanks to this feature, the vital parameter sensor may also be positioned at a location of the fastening device that does not usually come directly into contact with the skin of the user, but the vital parameter sensor comes into contact with an article of clothing of the user, preferably comes in contact with a protective clothing. This protective clothing is configured, as a rule, to protect the user from mechanical, chemical and/or thermal environmental effects, and it therefore has a sufficient thickness. The vital parameter sensor may be configured such that the electromagnetic waves can pass through the article of clothing without being greatly attenuated. A sensor that measures a vital parameter by being in contact with the skin cannot be positioned in such a location.

Since the vital parameter sensor or at least one vital parameter sensor measures a vital parameter in a contactless manner, the vital parameter sensor may also be positioned in the vicinity of the back or of a shoulder of the user. Therefore, the present invention makes it possible to arrange a plurality of vital parameter sensors in different positions relative to the body of the user. The present invention makes it possible as a result to provide a higher reliability in the measurement of the vital parameter as well as redundancy.

Since the vital parameter sensor measures the vital parameter by means of electromagnetic waves, the function of the vital parameter sensor does not depend, as a rule, on how thick an article of clothing is between the vital parameter sensor and the body of the user. The material of which the article of protective clothing is made is, as a rule, sufficiently transparent for electromagnetic waves. A vital parameter sensor measuring in a different manner could not measure through a thick article of clothing.

A sensor that comes directly into contact with the skin of the user is felt by the user as unpleasant or disturbing in some cases. A vital parameter sensor measuring in a contactless manner avoids this drawback.

In one embodiment, the vital parameter sensor or each vital parameter sensor measures a numerical value for the vital parameter. In another embodiment, the at least one vital parameter sensor delivers a signal, which enables a signal processing unit of the breathing air supply system or a signal processing unit located at a remote location in space automatically to decide whether the vital parameter value is within a predefined range or not. A value outside this range is an indicator of a current risk for the user. Based on the received signal, the signal processing unit is then able to trigger an alarm.

In a preferred embodiment, the vital parameter sensor or the at least one vital parameter sensor is configured as a distance sensor measuring in a contactless manner. The distance sensor is able to measure the distance between itself and a point in or at the body of the user, for example, at a point on the skin of the user. For example, the travel time of the electromagnetic waves is measured, and/or the Doppler effect is used.

The distance sensor is able to measure by repeated distance measurement a time curve of the distance between itself and the point in or at the body of the user. This time curve is correlated with the heart rate and/or the respiration rate of the user. Thanks to this embodiment, at least one important vital function of the user can therefore be measured in a non-invasive manner. The time curve of the distance, i.e., the change in the distance over time, is needed in order to measure the vital parameter, but the absolute value of the distance is not needed, as a rule. This absolute value may depend on the thickness of an article of protective clothing between the user and the sensor and is therefore unknown, but it is also not needed for the measurement, either.

This distance sensor is preferably configured as a radar sensor. This distance sensor preferably emits electromagnetic waves in a frequency spectrum in the range of 30 GHz to 300 Ghz.

The vital parameter sensor measuring in a contactless manner or each vital parameter sensor measuring in a contactless manner is arranged according to the present invention at or in the fastening device. In one embodiment, this fastening device comprises at least one cavity, i.e., a recess in the interior of the fastening device, which is enclosed by the fastening device from all sides. This cavity accommodates the vital parameter sensor or at least one vital parameter sensor, so that the fastening device fully encloses the vital parameter sensor. Thanks to this configuration, the fastening device protects the vital parameter sensor accommodated in the cavity to a certain degree from mechanical, chemical and/or thermal environmental effects. In addition, the risk of the vital parameter sensor performing relevant unintended movements relative to the body of the user is reduced to an even greater extent.

In a variant of this embodiment, this cavity is arranged in a back section of the fastening device, especially in a back plate. The back section and hence the vital parameter sensor in the cavity in the back section perform, as a rule, smaller movements relative to the body of the user than do other sections of the fastening device.

The vital parameter sensor measuring in a contactless manner or each vital parameter sensor measuring in a contactless manner is arranged according to the present invention at or in the fastening device. A plurality of vital parameter sensors are preferably arranged at different sections of the fastening device, especially at or in a back section, a shoulder strap section and/or a belly section. This embodiment leads to vital parameter sensors measuring different vital parameters or also the same vital parameter in different measuring positions. This provides intended redundancy. Even when an area of the fastening device is exposed to a high load, the risk of failure of all vital parameter sensors due to this load is low.

It is also possible that the vital parameter sensor measuring in a contactless manner or a vital parameter sensor measuring in a contactless manner is fastened at a part of the protective equipment and this part of the protective equipment is in contact with the head of the user, for example, it is integrated into a protective helmet or into a face mask.

The vital parameter sensor or each vital parameter sensor is arranged according to the present invention at or in the fastening device. In preferred embodiments of the vital parameter sensor, a relevant movement of a vital parameter sensor relative to the body of the user shall be prevented, for example, if the vital parameter sensor measures the changes over time in a distance to a point in or at the body of the user. In one embodiment, at least one movement-inhibiting element is mounted on a surface of the fastening device. This surface points towards the user. The movement-inhibiting element inhibits a movement of the fastening device and hence of at least one vital parameter sensor at or in the fastening device relative to the body of the user.

The movement-inhibiting element comprises, for example, an element made of rubber or another material with a high coefficient of friction, which comes into contact with an article of clothing, especially with an article of protective clothing, a user of the breathing air supply system wearing this article of clothing and carrying the fastening device on the article of clothing. The high friction between the movement-inhibiting element and the article of clothing reduces a possibly unintended relative movement.

An intended relative movement is reduced by means of a clamping element in one embodiment. This clamping element seeks to move the vital parameter sensor or at least one vital parameter sensor towards the body. As a result, the clamping element holds the vital parameter sensor in a prestressed position. When carrying the breathing air supply system, the user then applies a pressure to the vital parameter sensor against the force of the clamping element, doing so solely by carrying the fastening device, i.e., without any separate action.

The breathing air supply system preferably comprises a power supply unit of its own, so that the user can use the portable breathing air supply device independently from a stationary power supply. It is desirable for this power supply unit to need to release as little electrical energy as possible especially when the breathing air supply system is not currently being used. A breathing air supply system consumes electrical energy in order to emit electromagnetic waves.

The vital parameter sensor or at least one vital parameter sensor and preferably each vital parameter sensor can therefore preferably be operated optionally in a measuring state or in an inoperative state. The breathing air supply system consumes less electrical energy in the inoperative state than in the measuring state and it ideally consumes no electrical energy at all in the inoperative state. The vital parameter sensor is preferably in the measuring state only when the breathing air supply system is being used. In one embodiment, the breathing air supply system comprises a switch, by means of which the user can switch the electrical consumer of the breathing air supply system on and off.

In one preferred embodiment, the breathing air supply system comprises, by contrast, an automatic unit, which switches at least the vital parameter sensor or each vital parameter sensor off automatically when this is not needed. In one preferred embodiment, a use sensor is able to automatically detect whether the breathing air supply system is currently being carried by a user or else it is not currently being used. The use sensor detects, for example, the flow of breathing air in the breathing air supply system or a pressure that the user then applies to a contact switch or to a push switch when the user is carrying the breathing air supply system on his body. It is also possible that the use sensor detects whether an electrical connection is closed or interrupted, this electrical connection being closed when the breathing air supply system is being used.

The breathing air supply system preferably comprises a signal processing unit, which is arranged especially preferably at or in the fastening device. This signal processing unit receives signals from the use sensor via cable or in a wireless manner and decides automatically on the basis of these signals whether the breathing air supply system is currently being carried or not. The detection that the breathing air supply system is being carried triggers the step in which the signal processing unit brings the vital parameter sensor or each vital parameter sensor into a measuring state. As soon as the signal processing unit detects that the breathing air supply system is not being carried, it triggers the step of bringing the vital parameter sensor or each vital parameter sensor into the inoperative state. The signal processing unit preferably brings the vital parameter sensor into the inoperative state only when a predefined time period has elapsed after it had been detected that the breathing air supply system is not being carried. This embodiment reduces the risk that an incorrect signal of the use sensor leads to an unintended deactivation of the vital parameter sensor based on a short-term event.

In one embodiment, the vital parameter sensor or each vital parameter sensor delivers at least one signal each with a constant scanning frequency. In another embodiment, the scanning frequency of at least one vital parameter sensor can be changed from the outside when the vital parameter sensor is in the measuring state. A signal processing unit of the breathing air supply system is able to actuate the vital parameter sensor and bring about a change in the scanning frequency thereby. The signal processing unit is configured in one embodiment to increase the scanning frequency when the signal of this vital parameter sensor is outside a predefined normal range, which is an indicator of a possible risk for the user. The vital parameter is subsequently measured at an increased scanning frequency in this situation in order to rapidly clarify whether a risk is indeed present and/or in order to be able to rapidly detect a change in the signal over time. In one embodiment, the signal processing unit receives, in addition, signals from at least one environmental sensor, which measures an ambient condition, for example, the ambient temperature. If the ambient condition or a measured ambient condition is outside a predefined range, for example, if the temperature has exceeded a predefined temperature threshold, the signal processing unit will likewise increase the scanning frequency.

If the breathing air supply system has detected on the basis of a signal of a vital parameter sensor that at least one vital parameter is outside a predefined range, it preferably automatically triggers an alarm and outputs it in a form perceptible by a person. A signal processing unit of the breathing air supply system preferably receives signals from the vital parameter sensor or from each vital parameter sensor and compares these received signals with a respective predefined range per vital parameter being monitored. Or else, the vital parameter sensor itself analyzes its measured values and delivers an alarm signal when needed.

In one embodiment, the breathing air supply system comprises an output unit, which is capable of outputting an alarm in a form perceptible by a person. If the signal processing unit has detected that a measurable vital parameter is outside a predefined range, the signal processing unit actuates this output unit, and the actuated output unit outputs an alarm.

In one embodiment, the breathing air supply system comprises a communication unit, which is capable of transmitting messages to a receiver located remotely in space by means of radio waves. If the signal processing unit outputs an alarm, it preferably triggers the transmission of this alarm via the communication unit to the receiver located remotely in space. The receiver located remotely in space causes an output unit located remotely in space from the breathing air supply system to output this alarm in a form perceptible by a person. As a result, a person other than the user of the breathing air supply system is informed of the alarm and can initiate a rescue action. It is also possible that the signal processing unit transmits the measured value or each measured value of the vital parameter by means of the communication unit to the receiver located remotely in space. The receiver causes the output unit located remotely in space to output the vital parameter value received or each vital parameter value received in a form perceptible by a person, so that a person can monitor the vital functions of the user on the basis of the outputted vital parameter values.

The breathing air supply system is preferably configured in the manner of a backpack and can be carried by the user on his back and it can also be taken off. The fastening device can preferably be separated from the breathing air supply device, so that the fastening device can be cleaned separately. This is important for removing particles of harmful substances and harmful chemicals from the fastening device after a use.

The present invention will be described below on the basis of an exemplary embodiment. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF PREFERRED EMBODIMENTS

Figure 1:
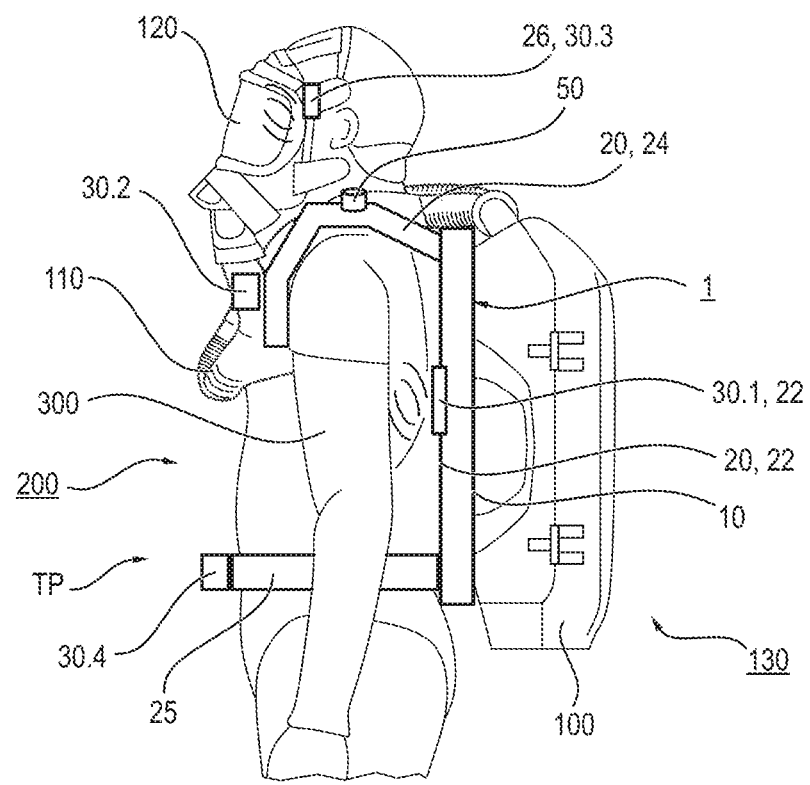
FIG. 1 is a side view of a preferred embodiment of a breathing air supply system according to the present invention.
Figure 2:
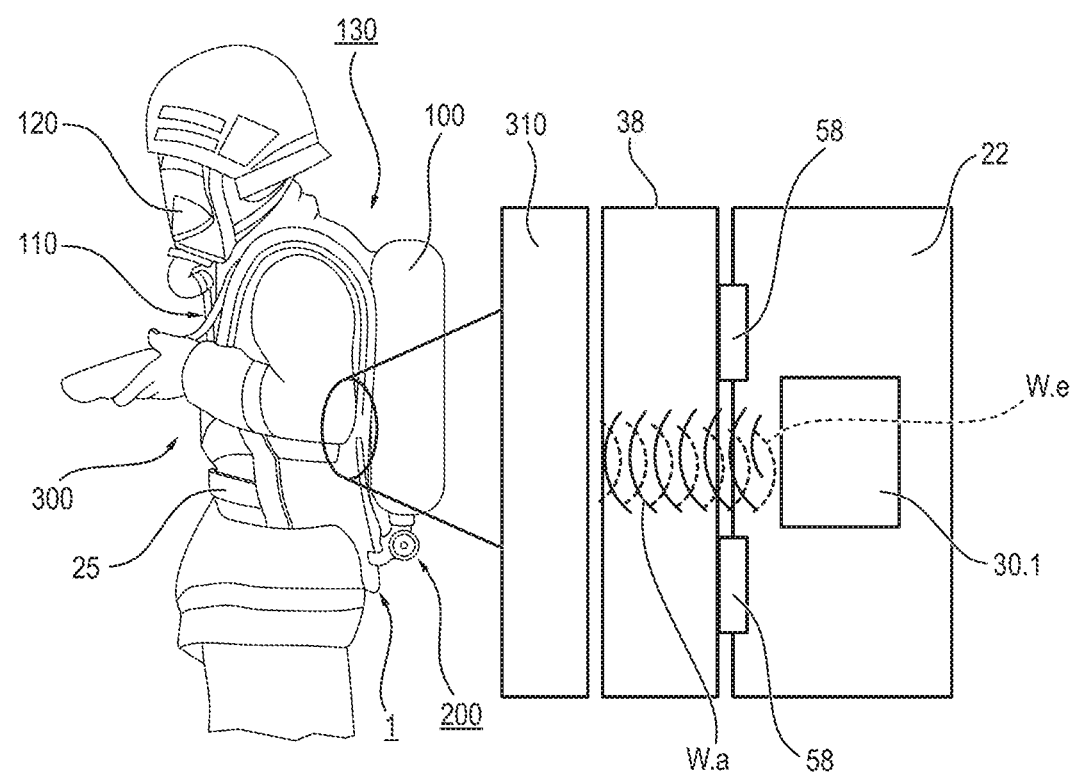
FIG. 2 is a side view with partial detail view showing how a vital parameter sensor is arranged in the back section of the fastening device according to FIG. 1.
Figure 3:
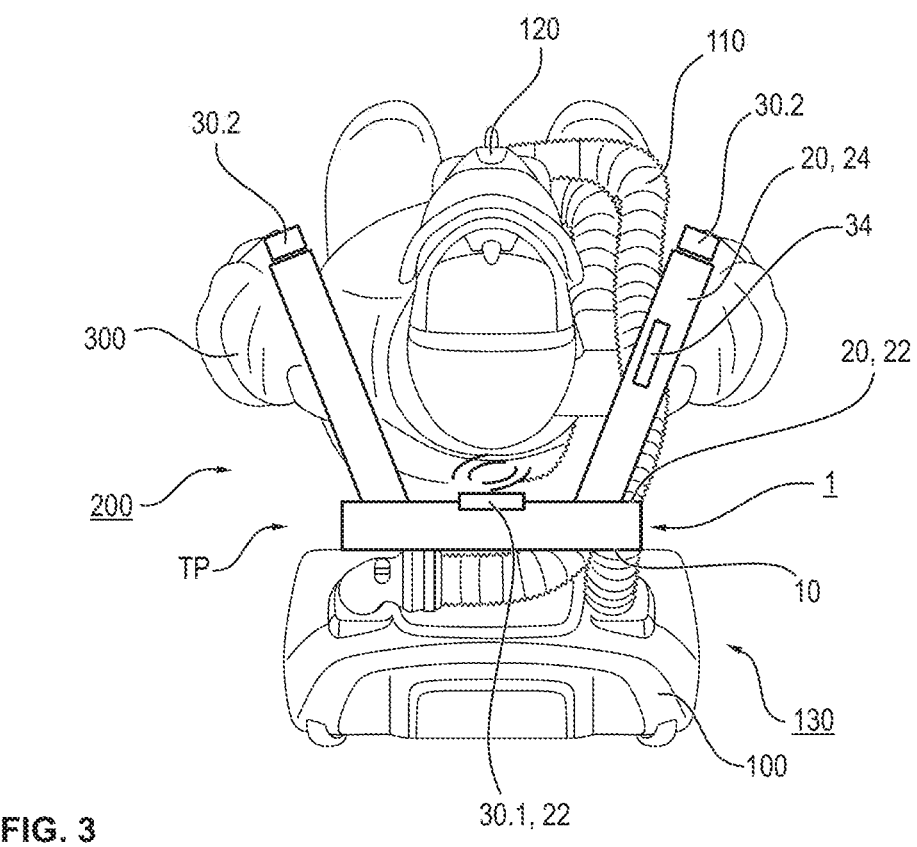
FIG. 3 is a top view of the preferred embodiment according to FIG. 1.

Referring to the drawings, FIG. 1 through FIG. 4 show a preferred embodiment of a breathing air supply system 200 according to the present invention, namely, in a side view (FIG. 1, FIG. 2 and FIG. 4) and in a top view (FIG. 3). The breathing air supply system 200 is carried by a person in a carrying position TP, this person being hereinafter called "the user 300." The breathing air supply system 200 comprises a breathing air supply device 130 as well as a fastening device 1. The breathing air supply device 130 comprises a storage tank 100 for breathing air,
a face piece 120, which surrounds the mouth and/or the nose of the user 300, doing so preferably in a fluid-tight manner, and
a plurality of air tubes 110, which connect the face piece 120 to the storage tank 100.

The user 300 can carry the storage tank 100 on his back in the manner of a backpack by means of the fastening device 1. The fastening device 1 preferably comprises a system comprising belts, straps, buckles and/or loops.

The fastening device 1 of the exemplary embodiment comprises
a mounting section 10 and
fastening section 20.

The fastening section 20 comprises
a back section 22, which is preferably in the form of a back plate, which is adapted to the shape of the back of the user 300,
a shoulder strap section 24,
a belly section 25 and
a head section 26, which is in contact with the head of the user 300.

The mounting section 10 carries the storage tank 100 and holds it on the back of the user 300. The fastening section 20 carries the mounting section 10. The sections 22, 24, 25 and 26 are in contact with the corresponding body parts of the user 300. The user 300 can carry and put down again the mounting section 10 by means of the fastening section 20.

At least one vital parameter sensor 30 is fastened to or in the fastening device 1. The vital parameter sensor 30 or each vital parameter sensor 30 measures a respective vital parameter VP of the user 300 and thereby provides a current vital parameter value. The vital parameter sensor 30 may carry out the measurement of the vital parameter VP continuously, for example, at a predefined scanning frequency, or at regular or irregular intervals. It is also possible that a measurement of the vital parameter VP is triggered by an actuation from the outside, also repeatedly, for example, regularly or in an event-controlled manner. A measurable vital parameter VP is correlated with a vital function, i.e., with a vitally necessary function of the user 300. Examples of such vital parameters are the respiration rate, heart rate, body temperature and skin temperature of the user 300.

The vital parameter sensor or each vital parameter sensor is fastened to or in the fastening device 1 or is integrated into same. As a result, the vital parameter sensor 30 or each vital parameter sensor 30 is located in the vicinity of the body of the user 300. The vital parameter sensor 30 or each vital parameter sensor 30 is preferably activated by the user 300 putting the fastening device 1 on his back. After its activation, each vital parameter sensor 30 is able to measure at least one respective vital parameter VP, without it being necessary for the user 300 to activate the vital parameter sensor 30 by an actuation. It is also possible that a vital parameter sensor 30 is activated continuously. The risk that a vital function is not measured because the user 300 has forgotten or deliberately chosen not to fasten the corresponding vital parameter sensor 30 to the fastening device 1 and/or to activate it or had deactivated it again is ruled out or at least reduced by both embodiments.

The vital parameter sensor 30 or each vital parameter sensor 30 measures a vital parameter VP in a contactless manner. Each vital parameter sensor 30 preferably comprises a transmitter and a receiver, especially a radar transmitter and a radar receiver. It is also possible that a transmitter emits infrared waves and a receiver receives reflected infrared waves. Based on its wavelength, hemoglobin in the human blood readily absorbs infrared waves, so that some vital parameters can be measured in this manner.

The transmitter emits electromagnetic waves in the direction of the body of the user 300, doing so preferably in a frequency spectrum in the range of 30 GHz to 300 GHz. The body reflects at least some of the emitted electromagnetic waves to the sensor, and the receiver receives the radio waves reflected from the body. The receiver preferably processes the received measured values, for example, by means of LNA, IF, ADC, PA, synthesization and/or Digital Front End, and delivers a signal.

Due to the respective travel time and/or to a phase difference being measured at each scan time, the current distance between the vital parameter sensor 30 and a point on the skin of the user 300 is measured with sufficient accuracy. This distance varies based on the heartbeat activity and/or the breathing activity of the user 300, depending on where the vital parameter sensor 30 is arranged. The changes over time in the distance are therefore correlated with the heartbeat activity and/or with the breathing activity.

A sensor, which is capable of measuring the heartbeat or the respiration rate or both rates of a living being, is described, for example, in US 2017/0 172 425 A1. The Doppler effect is used to determine the heart rate or the respiration rate. The vital parameter sensor 30 or at least one vital parameter sensor 30 at the fastening device 1 can thus be configured as is described there.

The embodiment with the vital parameter sensor 30 measuring in a contactless manner avoids the need for the user 300 to attach a sensor to his body. This necessity would imply the risk that the user 300 would forget to attach the sensor or that the sensor 30 would separate from the body of the user 300 during a use. The configuration with the vital parameter sensors 30 contactlessly measuring (measuring in a contactless manner) thus increases the reliability with which the vital functions of the user 300 are monitored.

The following vital parameter sensors 30 are fastened to or integrated into the fastening device 1 in the preferred embodiment:

- a vital parameter sensor 30.1, positioned at and in the back section 22,
- a vital parameter sensor 30.2, positioned at or in the shoulder strap section 24,
- a vital parameter sensor 30.3, positioned at or in the head section 26, and
- a vital parameter sensor 30.4, positioned at or in the belly section 25.

This embodiment provides redundancy, especially if the same vital parameter VP is measured by different vital parameter sensors 30. At least one vital parameter sensor 30 is preferably positioned in a corresponding recess or cavity of the fastening device 1; for example, sensor 30.1 is positioned in a cavity in the back section 22.

A first input/output unit 50 is optionally fastened at a shoulder strap section 24. This first input/output unit 50 is able to output at least one measured value of a vital parameter VP in a form perceptible by a person, especially optically and/or acoustically. In one embodiment, the input/output unit 50 is able, in addition, to detect user inputs. In one embodiment, it outputs the measured vital parameter value in a numeric form or graphically by means of a scale. In another embodiment, it outputs, in addition to the value or instead of the value, a rating, for example, by means of a traffic light function (green, yellow, red), or it outputs an alarm in a form perceptible by a person when a vital parameter assumes a critical value.

A signal processing unit 40, not shown in FIG. 1, which is likewise fastened to the fastening device 1, carries out the following steps in the exemplary embodiment:

- The signal processing unit 40 receives signals from the vital parameter sensor 30 or each vital parameter sensor 30. The vital parameter sensor 30 has optionally processed measured values and generated the signals.
- If the heartbeat activity and/or the respiration rate shall be measured, the received signals result from a superimposition of the heartbeat activity, the breathing activity and interference signals, i.e., they are sum signals. The signal processing unit determines from the received sum signals a cardiogenic signal, which is correlated with the heartbeat activity, and/or a respiratory signal, which is correlated with the breathing activity. The signal processing unit 40 preferably uses the respective position of a vital parameter sensor 30 at the fastening device 1 in order to determine the cardiogenic and/or respiratory signal.
- The signal processing unit 40 compares these received signals with predefined and stored ranges and then triggers an alarm if the measured value of at least one vital parameter VP is outside the respective predefined range.
- The process of triggering an alarm comprises the step in which the signal processing unit 40 actuates the first input/output unit 50 and the actuated first input/output unit 50 outputs the alarm in a form perceptible by a person. Thanks to this embodiment, an alarm is automatically triggered when at least one vital function of the user 300 enters into a range hazardous for a person. The user 300 himself as well as another member of the crew in the vicinity of the user 300 are able to perceive this alarm. The other member of the crew can rescue the user 300 if this is necessary.

The breathing air supply system 200 comprises an energy supply unit of its own, for example, a set of batteries. Each vital parameter sensor 30 can preferably be operated optionally in a measuring state or in an inoperative state. The vital parameter sensor 30 consumes less electrical energy in the inoperative state than in the measuring state, and it preferably consumes practically no energy in the inoperative state.

Each vital parameter sensor 30 operates in the measuring state with a scanning frequency and preferably delivers signals with this scanning frequency. In one embodiment, this scanning frequency remains constant as long as the vital parameter sensor 30 is in the measuring state. In another embodiment, this scanning frequency may change due to an actuation. The signal processing unit 40 preferably changes the scanning frequency of this vital parameter sensor by a corresponding actuation. The signal processing unit 40 preferably increases the scanning frequency if the vital parameter sensor 30 has delivered signals that are outside a predefined normal range, i.e., they indicate a possibly critical state of the user 300. In one embodiment, the signal processing unit 40 receives, in addition, signals from at least one environmental sensor, for example, from a temperature sensor, which measures the ambient temperature. If the measured ambient condition or a measured ambient condition is outside a normal range, the signal processing unit 40 increases the scanning frequency.

FIG. 2 shows in its left-hand part the user 300, who wears a protective clothing 38, which covers a large part of the skin 310 of the user 300 and is in contact with the skin 310. When the user 300 has additionally put on the breathing air supply system 200, the back section 22 of the fastening device 1 is in contact with the protective clothing. A vital parameter sensor 30.1 is arranged in a cavity in the interior of the back section 22. As a result, the back section 22 protects the vital parameter sensor 30.1 up to a certain degree from mechanical and chemical and thermal environmental effects. The emitted electromagnetic waves W.a as well as the reflected electromagnetic waves W.e are suggested.

The signals of the vital parameter sensor 30.1 would be distorted to a considerable extent if the vital parameter sensor 30.1 performed considerable movements relative to the skin 310 of the user 300. These relative movements are reduced in the exemplary embodiment by the protective clothing 38 being firmly in contact with the skin 310 of the user 300, by the fastening device 1 with the back section 22 being firmly in contact with the protective clothing 38 and by the vital parameter sensor 30.1 not being able to perform any relevant movements in the cavity relative to the back section 22. In one embodiment, elements 58 with a high coefficient of friction, for example, elements made of rubber, are applied to the surface of the back section 22 pointing towards the user 300 in order to further reduce the relative movement of the back section 22 relative to the protective clothing 38.

In one embodiment, the fastening device 1 comprises a clamping element, which acts on a vital parameter sensor 30, for example, a spring or an elastic bracket. When the user 300 is carrying the breathing air supply system 200, this clamping element seeks to press the vital parameter sensor 30 against the user 300. As a result, the vital parameter sensor 30 is pressed against the protective clothing 38. This embodiment also reduces the risk of the vital parameter sensor 30 performing an undesired movement relative to the skin 310 of the user 300.

FIG. 3 shows the preferred embodiment of the breathing air supply system 200 from FIG. 1 and FIG. 2 in a top view. Identical components are designated by the same reference numbers as in FIG. 1 and FIG. 2. A use sensor 34 is fastened to the fastening device 1 or is integrated into same, into the shoulder strap section 24 in the example being shown. The use sensor 34 is able to detect whether the user 300 is currently carrying the fastening device 1 and hence the breathing air supply system 200 or not. The use sensor 34 comprises, for example, a contact switch or a push switch or a switch that checks whether an electrical connection is opened or closed, this connection being closed when the user 300 is carrying the breathing air supply system 200. It is also possible that the use sensor 34 checks whether the user 300 is drawing breathing air from the storage tank 100 and/or whether breathing air is flowing from the storage tank 100.

The signal processing unit 40 receives signals from the use sensor 34. The vital parameter sensor 30 or each vital parameter sensor 30 is in an inoperative state as long as the signal processing unit 40 has detected on the basis of signals—or on the basis of the lack of signals—of the use sensor 34 that the fastening device 1 is not being carried. As soon as the signal processing unit 40 has detected that the fastening device 1 is being carried, the signal processing unit 40 activates the vital parameter sensor 30 or each vital parameter sensor 30 and brings it therefore into a measuring state. This embodiment saves energy, because the vital parameter sensor 30 or each vital parameter sensor 30 is deactivated and is in an energy-saving inoperative state as long as it is not needed. Thanks to the use sensor 34, it is not necessary for the user 300 or another person to switch on the vital parameter sensor 30 or each vital parameter sensor 30 or to otherwise activate it. In addition, the signal processing unit 40 is able to detect the result that the vital parameter sensor 30 or each vital parameter sensor 30 is defective and therefore it is not delivering any signals, and then to cause the first input/output unit 50 to output a corresponding message.

Figure 4:
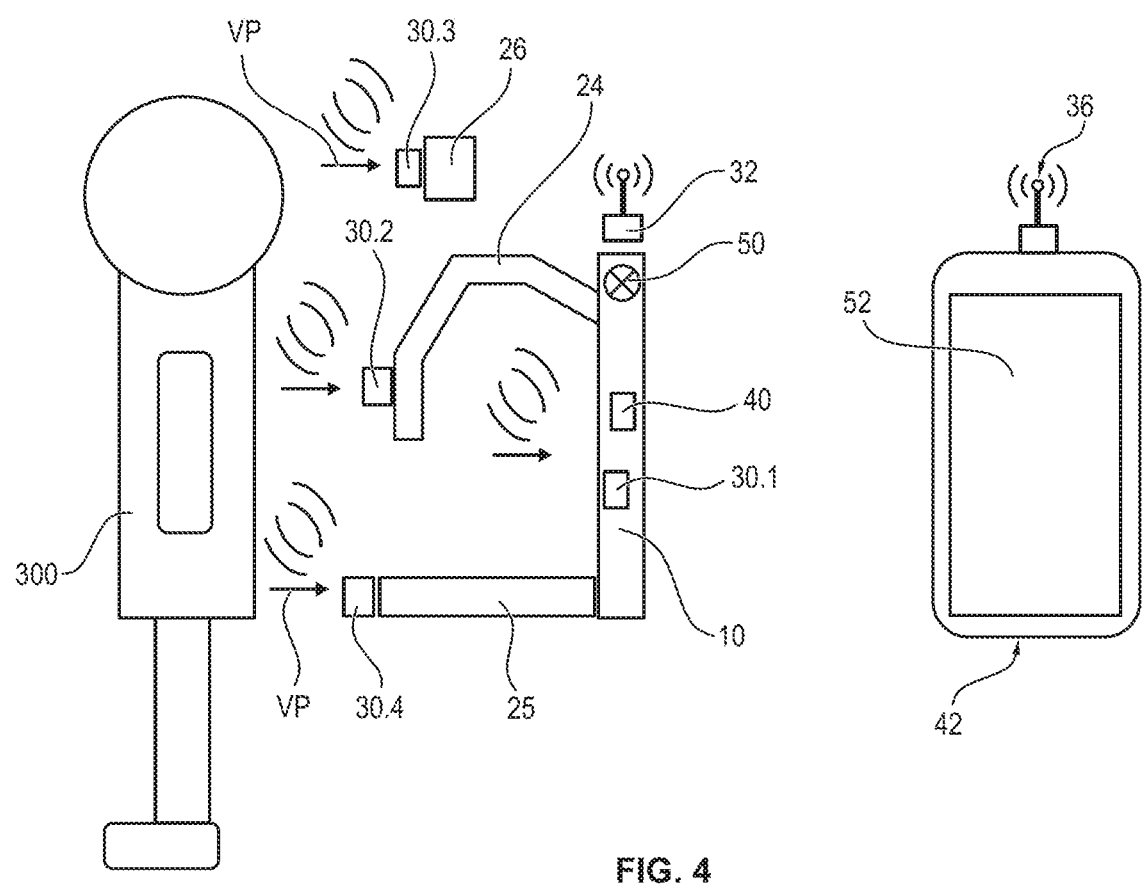
FIG. 4 is a schematic in a side view showing the integration of the breathing air supply system of FIG. 1 and FIG. 3 in a data network.

FIG. 4 schematically shows in a side view the integration of the breathing air supply system according to the preferred embodiment shown in FIG. 1 and in FIG. 3 in a data network. FIG. 4 shows the following components of the breathing air supply system 200, which is carried by the user 300 in a carrying position TP:

four exemplary vital parameter sensors 30.1, . . . , 30.4 at the sections 10, 22, . . . ,
the above-mentioned signal processing unit 40 at or in the fastening device 1 and
a communication unit 32.

The vital parameter sensors 30.1, . . . , 30.4 measure values of a respective vital parameter VP each of the user 300, which are determined in a contactless manner. The signals of the vital parameter sensors 30.1, . . . , 30.4 are transmitted to the signal processing unit 40 via cable or by means of radio waves. The signal processing unit 40 analyzes these signals and actuates the first input/output unit 50 when needed. In addition, the signal processing unit 40 triggers the step of transmitting measured and processed signals concerning the vital parameters VP to the communication unit 32 and of being emitted by this.

In one embodiment, the user 300 uses headphones or speakers as well as a microphone. Verbal messages can therefore be outputted for the user 300, and the user 300 can input verbal messages. These verbal messages are likewise transmitted in one embodiment by means of the communication unit 32.

A central computer 42 is located at a spaced location from the fastening device 1 and hence also from the signal processing unit 40. The central computer 42 is preferably a portable computer, for example, a smartphone, and is carried and used by a head of operations, said head of operations monitoring the user 300 and other members of the rescue crew and initiating a rescue action for a rescue crew member when needed.

A second communication unit 36, which is in a data connection by means of radio waves with the first communication unit 32 and optionally with additional communication units of other users at least at times, is fastened to the central computer 42. In addition, the central computer 42 comprises a second input/output unit 52. The signal processing unit 40 transmits measured vital parameter values of the user 300 via the communication units 32 and 36 to the central computer 42. The central computer 42 displays the received vital parameter values in one embodiment in a form perceptible by a person on the second input/output unit 52, for example, as numerical values and/or graphically on a scale. In one embodiment, the central computer 42 detects a user input and triggers the step of transmitting a message to the user 300. The user 300 is prompted with this message to carry out a user input into the first input/output unit 50.

The central computer 42 likewise triggers an alarm if a transmitted vital parameter value is outside the predefined range or if the central computer 42 does not receive a corresponding user input from the user 300. The step of triggering an alarm comprises the step in which the central computer 42 actuates the second input/output unit 52 and prompts the second input/output unit 52 to output an alarm in a form perceptible by a person.

In addition, the central computer 42 is able to poll the signal processing unit 40 regularly and/or after a corresponding user input and to prompt the transmission of vital parameter values from the signal processing unit 40 to the central computer 42. As a result, it is possible, in particular, to check from a distance in space whether the signal processing unit 40 and the first communication unit 32 are still able to function or not.

While specific embodiments of the invention have been shown and described in detail to illustrate the application of the principles of the invention, it will be understood that the invention may be embodied otherwise without departing from such principles.

REFERENCE CHARACTERS

1 Fastening device, comprises the mounting section 10, the fastening section 20 and the vital parameter sensor 30 or each vital parameter sensor 30
10 Mounting section
20 Fastening section, comprises the sections 22, 24 and 25
22 Back section, belongs to the fastening section 20
24 Shoulder strap section, belongs to the fastening section 20
25 Belly section, belongs to the fastening section 20
26 Head section
30 Vital parameter sensor
30.1 Vital parameter sensor, positioned at or in the back section 22
30.2 Vital parameter sensor, positioned at or in the shoulder strap section 24

30.3 Vital parameter sensor, positioned at or in the head section 26
30.4 Vital parameter sensor, positioned at or in the belly section 25
32 First communication unit, fastened to the fastening device 1
34 Sensor for detecting whether the user 300 is currently carrying the breathing air supply system 200 or not
36 Second communication unit, fastened to the central computer 42
38 Protective clothing, which is in contact with the skin 310 of the user 300 and protects the user 300
40 Signal processing unit of the breathing air supply system 200, receives signals from the vital parameter sensor 30 or from each vital parameter sensor 30 and actuates the first input/output unit 50
42 Central computer, comprises the second communication unit 36 and the second input/output unit 52
50 First input/output unit, fastened to the fastening device 1
52 Second input/output unit, belongs to the central computer 42
58 Movement-inhibiting elements on the surface of the back section 22 pointing towards the user 300; they reduce a relative movement of the vital parameter sensor 30.1 relative to the protective clothing 38
100 Storage tank for breathing air, belongs to the breathing air supply device 130
110 Air tubes; they connect the storage tank 100 to the face piece 120; belong to the breathing air supply device 130
120 Face piece; belongs to the breathing air supply device 130
130 Breathing air supply device; belongs to the breathing air supply system 200; comprises the storage tank 100 for breathing air, air tubes 110 and a face piece 120
200 Breathing air supply system; comprises the breathing air supply device 130 and the fastening device 1
300 User of the breathing air supply system 200
310 Skin of the user 300, partially covered by the protective clothing 38
TP Carrying position: The breathing air supply system 200 is being carried by a user 300
VP Measured vital parameters of the user 300
W.a Electromagnetic waves emitted by the vital parameter sensor 30.1
W.e Electromagnetic waves reflected by the body of the user 300

The invention claimed is:

1. A breathing air supply system to be carried by a user, the breathing supply system comprising:
    a breathing air supply device;
    a fastening device configured to be in contact with the body of the user of the breathing air supply system and to carry the breathing air supply device; and
    a vital parameter sensor fastened at or in the fastening device or integrated into the fastening device, the vital parameter sensor being arranged to be in contact with clothing of the user, wherein:
        the vital parameter sensor is configured to measure at least one vital parameter of the user of the breathing air supply system; and
        the vital parameter sensor is configured to emit electromagnetic waves in a direction of the body of a user of the breathing air supply system, to receive electromagnetic waves reflected from the body of the user and to measure the respective vital parameter as a function of the received electromagnetic waves.

2. A breathing air supply system in accordance with claim 1, wherein the vital parameter sensor is configured as a distance sensor measuring contactlessly.

3. A breathing air supply system in accordance with claim 1, wherein:
    the fastening device comprises at least one cavity; and
    the vital parameter sensor is arranged in the cavity and is completely enclosed by the fastening device.

4. A breathing air supply system in accordance with claim 1, wherein:
    the fastening device comprises a back section, or a shoulder strap section or a belly section, or any combination of a back section and a shoulder strap section and a belly section; and
    the vital parameter sensor is arranged in or at the back section or in or at the shoulder strap section or in or at the belly section.

5. A breathing air supply system in accordance with claim 1, further comprising a movement-inhibiting element mounted on a surface of the fastening device, which surface points towards the user, and which movement-inhibiting element is configured to reduce a movement of the fastening device relative to the user.

6. A breathing air supply system in accordance with claim 1, wherein the fastening device comprises at least one clamping element configured to bias the vital parameter sensor in the direction of the user of the breathing air supply system and to hold as a result the vital parameter sensor in a prestressed position.

7. A breathing air supply system in accordance with claim 1, wherein:
    the breathing air supply system comprises a use sensor, which is configured to automatically detect whether the breathing air supply system is being carried by the user or is not being carried by the user, and the vital parameter sensor may be in a measuring state or in an inoperative state; and
    the breathing air supply system is configured to bring the vital parameter sensor into the measuring state in response to the use sensor detecting that the breathing air supply system is being carried, and/or to bring the vital parameter sensor into the inoperative state when the use sensor has detected that the breathing air supply system is not being carried.

8. A breathing air supply system in accordance with claim 1, further comprising a signal processing unit, wherein:
    the vital parameter sensor has a variable scanning frequency; and
    the signal processing unit is configured to automatically change the scanning frequency of the vital parameter sensor as a function of signals of the vital parameter sensor and/or of another signal of the breathing air supply system and/or as a function of signals of an ambience sensor, which measures an ambient condition.

9. A breathing air supply system in accordance with claim 1, further comprising a communication unit configured to transmit by means of radio waves one or more value that has been measured by the vital parameter sensor to a receiver located remotely in space.

10. A breathing air supply system in accordance with claim 2, wherein the distance sensor is configured as a radar sensor and is configured to emit electromagnetic waves in a frequency spectrum in the range of 30 GHz to 300 GHz.

11. A breathing air supply system in accordance with claim 4, further comprising another vital parameter sensors to provide a plurality of vital parameter sensors, wherein the plurality of vital parameter sensors are arranged at or in at least two different sections of the fastening device.

12. A breathing air supply system in accordance with claim 8, wherein the signal processing unit is configured to automatically change the scanning frequency of the vital parameter sensor as a function of signals of an ambience sensor, which measures an ambient condition.

13. A breathing air supply system in accordance with claim 1, wherein:
the vital parameter sensor is in contact with the clothing of the user in the direction of the body of the user.

14. A breathing air supply system to be carried by a user, the breathing supply system comprising:
a breathing air supply device;
a fastening device configured to be in contact with the body of the user of the breathing air supply system and to carry the breathing air supply device; and
a vital parameter sensor fastened at or in the fastening device or integrated into the fastening device, wherein:
the vital parameter sensor is configured to measure at least one vital parameter of the user of the breathing air supply system; and
the vital parameter sensor is configured to emit electromagnetic waves in a direction of the body of a user of the breathing air supply system, to receive electromagnetic waves reflected from the body of the user and to measure the respective vital parameter as a function of the received electromagnetic waves, the fastening device comprising at least one clamping element configured to bias the vital parameter sensor in the direction of the user of the breathing air supply system and to hold as a result the vital parameter sensor in a prestressed position.

15. A breathing air supply system to be carried by a user, the breathing supply system comprising:
a breathing air supply device;
a fastening device configured to be in contact with the body of the user of the breathing air supply system and to carry the breathing air supply device, the fastening device having a back section configured to be in contact with a back of the user of the breathing air supply system, the fastening device comprises at least one cavity arranged in the back section; and
a vital parameter sensor fastened at or in the fastening device or integrated into the fastening device, the vital parameter sensor being arranged to be in contact with clothing of the user, wherein:
the vital parameter sensor is configured to measure at least one vital parameter of the user of the breathing air supply system;
the vital parameter sensor is configured to emit electromagnetic waves in a direction of the body of a user of the breathing air supply system, to receive electromagnetic waves reflected from the body of the user and to measure the respective vital parameter as a function of the received electromagnetic waves;
the vital parameter sensor is arranged in the cavity and is completely enclosed by the fastening device.

* * * * *